US000001952H

(19) United States

(12) Statutory Invention Registration (10) Reg. No.: US H1952 H

Reed et al. (43) Published: Mar. 6, 2001

(54) MECHANICAL RESTORATION OF A DEFORMED LOOP STRUCTURE

(75) Inventors: Brendan Christopher Reed, Cincinnati; William Joseph Toerner, Wyoming, both of OH (US)

(73) Assignee: The Procter & Gamble Company, Cincinnati, OH (US)

(21) Appl. No.: 09/092,200

(22) Filed: Jun. 5, 1998

(51) Int. Cl.[7] ..... A61F 13/15; G03B 1/18

(52) U.S. Cl. ..... 604/391; 604/385.1; 226/52

(58) Field of Search ..... 604/391, 385.1; 226/52

(56) References Cited

U.S. PATENT DOCUMENTS

| | | | | |
|---|---|---|---|---|
| 4,782,988 | | 11/1988 | Nishiyama | 226/52 |
| 4,894,060 | * | 1/1990 | Nestegard | 604/391 |

FOREIGN PATENT DOCUMENTS

| | | |
|---|---|---|
| 1 182 436 | 6/1959 | (FR) . |
| 2 767 653 | 3/1999 | (FR) . |
| WO 94/23609 | 10/1994 | (WO) . |

* cited by examiner

*Primary Examiner*—Charles T. Jordan
*Assistant Examiner*—Aileen J. Baker
(74) *Attorney, Agent, or Firm*—Monte D. Witte; Steven W. Miller; Jacobus C. Rasser

(57) ABSTRACT

An improved process for making disposable diapers, and the like, having hook-and-loop fastening systems, and disposable diapers made by the improved process. The loop structure of the hook-and-loop fastening system used in this invention is substantially free of article attachment adhesive and comprises loop elements affixed to a support structure. The loop elements are deformed when the loop structure is wound onto a parent roll. At least a portion of the deformed loop elements are restored to essentially their original, undeformed, state after the loop structure is unwoundfrom the parent roll. The restoration is accomplished by contacting the loop elements with a mechanical restoration device which comprises either a brush or a scarfing surface. The brush preferably has a plurality of bristles having an average free length greater than about three times the average undeformed height of the loop elements and an average bending modulus less than the average modulus of elasticity of the loop elements. The scarfing surface preferably has an average roughness of at least about 500 RMS.

8 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MECHANICAL RESTORATION OF A DEFORMED LOOP STRUCTURE

BACKGROUND OF THE INVENTION

1. Field of the Invention

This invention relates to hook-and-loop fastening systems. More particularly, it relates to manufacturing processes for articles comprising hook-and-loop fastening systems. Even more particularly, it relates to an improvement in continuous processes for the attachment of loop structures of hook-and-loop fastening systems to articles of manufacture.

2. Background Art

The general public, frequently erroneously, refers to the ubiquitous hook-and-loop fastening system as "Velcro®" regardless of the manufacturer or the technical form of the system. The various hook-and-loop fastening systems have found extensive use wherever repeated attachment and reattachment, fastening and unfastening are required. Articles of clothing such as jackets and shoes commonly use hook-and-loop systems. One major use of hook-and-loop systems is in disposable diapers. (In this particular application the hook-and-loop system is sometimes called a "mechanical fastening" system.) While the present invention can be used in a wide variety of applications, and while its use in such wide variety is not disclaimed, for the sake of simplicity it will be discussed and described in conjunction with its use in the manufacture of disposable diapers.

There are numerous patents in which various hook-and-loop systems are described as well as patents in which various methods of affixing the hook-and-loop systems to disposable diapers are described.

Examples of patents describing hook-and-loop systems include U.S. Pat. No. 4,846,815 issued to Scripps on Jul. 11, 1989; U.S. Pat. No. 4,894,060 issued to Nestegard on Jan. 16, 1990; and U.S. Pat. No. 4,973,326 issued to Wood et al on Nov. 27, 1990.

Examples of patents describing disposable diapers which can benefit from use of the present invention include U.S. Pat. No. 3,860,003 issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; each of which is incorporated herein by reference. It will be clear to those skilled in the art that other diaper structures can also benefit from use of the present invention.

SUMMARY OF THE INVENTION

This invention is of an improvement in continuous processes for manufacturing articles comprising hook-and-loop fastening systems. The improvement comprises the steps of:

a.) Providing a loop structure comprising a plurality of loop elements, the loop elements being affixed to a support substrate, the support substrate being substantially free of article attachment adhesive;

b.) Deforming at least a portion of the loop elements by winding the loop structure upon itself to form a parent roll;

c.) Unwinding the loop structure from the parent roll;

d.) Restoring at least a portion of the deformed loop elements by contacting the deformed loop elements with a mechanical restoration device; and e.) Introducing the loop structure comprising the restored loop elements into the continuous process.

The restoration device can be a brush having particular properties or a solid surface having specified roughness characteristics.

BRIEF DESCRIPTION OF THE DRAWINGS

To aid in the understanding of the invention, the following non-limiting drawings are presented. The thickness of certain materials has been exaggerated for clarity.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings and example.

This invention is of an improvement in continuous processes for manufacturing articles comprising hook-and-loop fastening systems. The improvement comprises the steps of:

a.) Providing a loop structure comprising a plurality of loop elements, the loop elements being affixed to a support substrate, and the support substrate being substantially free of article attachment adhesive;

b.) Deforming at least a portion of the loop elements by winding the loop structure upon itself to form a parent roll;

c.) Unwinding the loop structure with its deformed loop structures from the parent roll;

d.) Restoring at least a portion of the deformed loop elements by contacting the deformed loop elements with a mechanical restoration device; and e.) Introducing the loop structure comprising the restored loop elements into the continuous process.

The restoration device can be a brush having particular properties or a solid surface having specified roughness characteristics.

Figure 1:
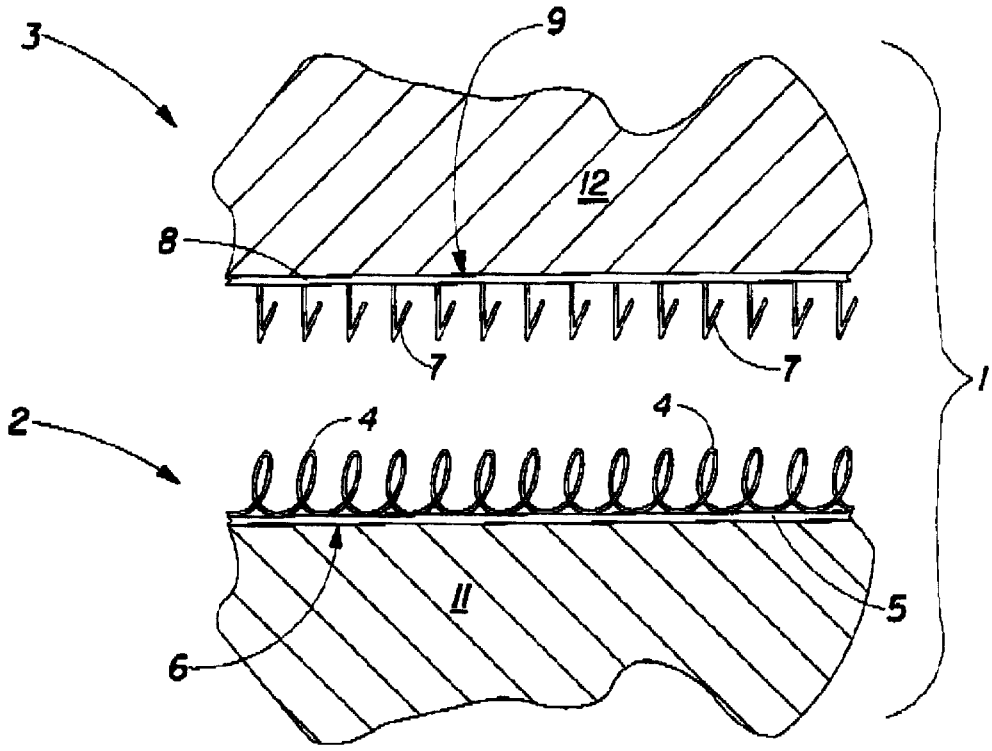
FIG. 1 is a cross sectional view of a generic hook-and-loop fastening system. It is intended to represent a wide variety of such systems while not illustrating any one system with particularity. In this illustration the hooks are not engaged with the loops.

FIG. 1 is a cross sectional view of generic hook-and-loop fastening system 1. As noted above, illustrated fastening system 1 is intended to represent a wide variety of such systems while not illustrating any one system with particularity. U.S. Pat. Nos. 4,846,815; 4,894,060; and 4,973,326 mentioned above, and which are incorporated herein by reference, describe hook structures, loop structures, and hook-and-loop fastening systems which can be used in the present invention. Additional references describing hook structures and loop structures include U.S. Pat. No. 5,019,073 issued to Roessler et al on May 28, 1991; U.S. Pat. No. 5,318,555 issued to Siebers et al on Jun. 7, 1994; and PCT Publication WO 96/13996 issued to Thomas on May 17, 1996. All the foregoing references are incorporated herein by reference.

Hook-and-loop fastening system 1 comprises loop structure 2 and hook structure 3. Loop structure 2, in turn, comprises a plurality of loop elements 4 affixed (by means not shown) to loop support substrate 5. Hook structure 3, in turn, comprises hook elements 7 affixed (by means not shown) to hook support substrate 8. In this cross sectional view, hooks 7 are shown disengaged from loop element 4. It is to be understood that when fastening system 1 is in use, hooks 7 cooperate with loop element 4 to effect releasable union of structures 2 and 3. Reference numerals 6 and 9 indicate, respectively, loop structure attachment surface and hook structure attachment surface. Loop structure 2 will, in use, be affixed at attachment surface 6 to an article of manufacture 11. Hook structure 3 will, in use, be affixed at attachment surface 9 to an article of manufacture 12. In this orientation, then, fastening system 1 can be used to releasable join the two articles of manufacture 11 and 12. Alternatively, articles of manufacture 11 and 12 can be envisioned as being different parts of the same overall article of manufacture. In this orientation, then, fastening system 1 can be used to releasable secure the two parts of the overall article to one another.

Figure 2:
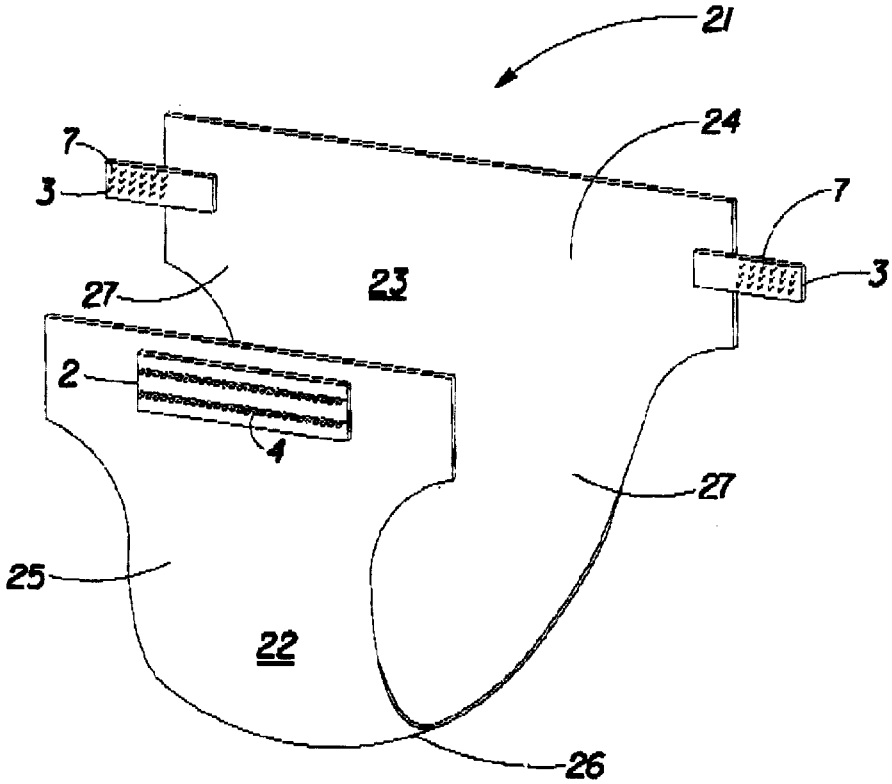
FIG. 2 is a perspective view of a generic disposable diaper and illustrates a significant use of the hook-and-loop fastening system used with the present invention. It is intended to represent a wide variety of disposable diapers while not illustrating any one disposable diaper with particularity.

FIG. 2 is a perspective view of simplistic, generic disposable diaper 21. As noted above, illustrated disposable diaper 21 is intended to represent a wide variety of such disposable diapers while not illustrating any one diaper with particularity. U.S. Pat. Nos. 3,860,003, 5,151,092, and 5,221,274 mentioned above and incorporated herein by reference, describe disposable diapers which can benefit from the use of the present invention. The present invention, however, finds application in other diaper designs.

Diaper 21 comprises outer liquid impermeable backsheet 22 and inner liquid permeable topsheet 23. An absorbent element, not illustrated, is interposed between backsheet 22 and topsheet 23. Hook structures 3 are affixed to rear portion 24 of diaper 21 by means not illustrated. In this position, loop structure 2 provides what those skilled in the art sometimes refer to as a "landing zone" for hook elements 7 of hook structures 3. Hook structures 3 are affixed to diaper 21 with a plurality of hook elements 7 oriented as shown. Loop structure 2 is affixed to front portion 25 of diaper 21 by means not illustrated. A plurality of loop elements 4 are oriented as shown. In use, diaper 21 is applied to a human wearer, such as an infant, by placing crotch region 26 of diaper 21 between the legs of the wearer with front portion 25 adjacent the front of the wearer and rear portion 24 adjacent the back of the wearer. Each rear side margin 27 is then folded about the hips and thighs of the wearer. Hook elements 7 are engaged with loop elements 4 to secure diaper 21 in position about the wearer.

Backsheet 22 is impervious to liquids (e.g., urine) and comprises, for example, a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials can include breathable materials which permit vapors to escape from the diaper 21 while still preventing exudates from passing through the backsheet 22. Exemplary breathable materials include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT application No. WO 95/16746, published on Jun. 22, 1995 in the name of E.I. DuPont and copending U.S. patent application Ser. No. 08/744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of the foregoing references is incorporated herein by reference.

The whole of backsheet 22, or any portion thereof, can be elastically extensible in one or more directions. Extensible webs suitable for the present invention are described in U.S. Pat. No. 5,518,801 issued to Chappell, et, al. on May 21, 1996, which is incorporated herein by reference. In alternate embodiments, backsheet 22 comprises elastomeric films, foams, strands, or combinations of these or other suitable materials with nonwovens or synthetic films.

The present invention is not dependent on the use of any particular backsheet. The foregoing is presented for purposes of illustration and not limitation.

Topsheet 23 is preferably compliant, soft feeling, and non-irritating to the wearer's skin. Further, at least a portion of topsheet 23 is liquid pervious, permitting liquids to readily penetrate through its thickness. Topsheet 23 can be manufactured from a wide range of materials such as porous foams; reticulated foams; formed plastic films such as apertured plastic films;, and woven or nonwoven webs of natural fibers (e.g., wood or cotton fibers), synthetic fibers (e.g., polyester or polypropylene fibers), or a combination of natural and synthetic fibers. If topsheet 23 includes fibers, the fibers can be spunbond, carded, wet-laid, meltblown, hydroentangled, or otherwise processed as is well known in the art. One suitable topsheet material comprises a web of staple length polypropylene fibers and is manufactured by Veratec, Inc., a Division of International Paper Company, of Walpole, Mass. under the designation P-8.

Formed films suitable for topsheet 23 are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel, et al. on Aug. 3, 1982; U.S. Pat. No. 4,463,045 issued to Ahr, et al. on Jul. 31, 1984; and U.S. Pat. No. 5,006,394 issued to Baird on Apr. 9, 1991. Other suitable topsheets can be made in accordance with U.S. Pat. Nos. 4,609,518 and 4,629,643 which issued to Curro et al. on Sep. 2, 1986 and Dec. 16, 1986, respectively. All of the foregoing patents are incorporated herein by reference. Suitable formed films are available from The Procter & Gamble Company of Cincinnati, Ohio as "DRI-WEAVE" and from Tredegar Corporation of Terre Haute, Ind. as "CLIFF-T."

Preferably, topsheet 23 is made of a hydrophobic material or is treated so as to be hydrophobic in order to isolate the wearer's skin from liquids contained in the absorbent element. If topsheet 23 is made of a hydrophobic material, preferably at least the upper surface of topsheet 23 is treated to be hydrophilic so that liquids will transfer through the topsheet more rapidly. This diminishes the likelihood that body exudates will flow off topsheet 23 rather than being drawn through topsheet 23 and being absorbed by the absorbent element. Topsheet 23 can be rendered hydrophilic by treating it with a surfactant or by incorporating a surfactant into the topsheet material. Suitable methods for treating topsheet 23 with a surfactant include spraying topsheet 23 with the surfactant and immersing the material into the surfactant. A more detailed discussion of such a treatment and hydrophilicity is contained in U.S. Pat. Nos. 4,988,344 and 4,988,345 issued to Reising, et al. on Jan. 29, 1991. A more detailed discussion of suitable methods for incorporating surfactant in the topsheet can be found in U.S. Statutory Invention Registration No. H1670, published on Jul. 1, 1997 in the names of Aziz et al. Each of the foregoing references is incorporated herein by reference. Alternatively, topsheet 23 can include an apertured web or film which is hydrophobic. This can be accomplished eliminating the hydrophilizing treatment step from the production process or by applying a hydrophobic treatment to topsheet 23. Materials such as polytetraflouroethylene compounds and a hydrophobic lotion composition (as described below) are suitable. In such embodiments, it is preferred that the apertures be large enough to allow the penetration of aqueous fluids like urine without significant resistance.

Any portion of topsheet 23 can be coated with a lotion as is known in the art. Examples of suitable lotions include those described in U.S. Pat. No. 5,607,760 issued to Roe on Mar. 4, 1997; U.S. Pat. No. 5,609,587 issued to Roe on Mar. 11, 1997; U.S. Pat. No. 5,635,191 issued to Roe et al. on Jun. 3, 1997; and U.S. Pat. No. 5,643,588 issued to Roe et al. on Jul. 1, 1997. The lotion can function alone or in combination with another agent as the hydrophobizing treatment described above. The topsheet can also include or be treated with antibacterial agents, examples of which are disclosed in PCT Publication No. WO 95/24173 published on Sep. 14, 1995 in the name of Johnson. Further, the whole of topsheet 23, the whole of backsheet 22 or any portion of either can be embossed or matte finished to provide a more cloth like appearance.

The present invention is not dependent on the use of any particular topsheet. The foregoing is presented for purposes of illustration and not limitation.

The absorbent element, which is mentioned above and which, as noted, is not illustrated in FIG. 2, comprises any absorbent material which is generally compressible, conformable, non-irritating to the wearer's skin, and capable of absorbing and retaining liquids such as urine and other certain body exudates. The absorbent element can be manufactured in a wide variety of sizes and shapes (e.g., rectangular, hourglass, "T"-shaped, asymmetric, etc.) dependent on the overall diaper design, and can comprise a wide variety of liquid-absorbent materials commonly used in disposable diapers such as, for example, comminuted wood pulp generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; and any other known absorbent material or combinations of materials.

The configuration and construction of the absorbent element can be varied (e.g., the absorbent element or other absorbent structure can have varying caliper zones, a hydrophilic gradient, a superabsorbent gradient, or lower average density and lower average basis weight acquisition zones; or can comprise one or more layers or structures). However, the total absorbent capacity of the absorbent element should be compatible with the design loading and the intended use of diaper 21.

Exemplary absorbent structures for use as the absorbent element are described in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,834,735 issued to Alemany et al. on May 30, 1989; U.S. Pat. No. 4,888,231 issued to Angstadt on Dec. 19, 1989; U.S. Pat. No. 5,137,537 issued to Herron et al. on Aug. 11, 1992; U.S. Pat. No. 5,147,345 issued to Young et al. on Sep. 15, 1992; U.S. Pat. No. 5,342,338 issued to Roe on Aug. 30, 1994; U.S. Pat. No. 5,260,345 issued to DesMarais et al. on Nov. 9, 1993; U.S. Pat. No. 5,387,207 issued to Dyer et al. on Feb. 7, 1995; and U.S. Pat. No. 5,650,222 issued to DesMarais et al. on Jul. 22, 1997. Each of these patents is incorporated herein by reference.

The present invention is not dependent on the use of any particular absorbent element. The foregoing are presented for purposes of illustration and not limitation.

Backsheet 22 can be joined to topsheet 23, the absorbent element or any other element of diaper 21 by any attachment means known in the art. For example, the attachment means can include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of the foregoing patents is incorporated herein by reference. Adhesives which have been found to be satisfactory are manufactured by H. B. Fuller Company of St. Paul, Minn. and marketed as HL-1620 and HL-1358-XZP. Alternatively, the attachment means can comprise heat bonds, pressure bonds, ultrasonic bonds, dynamic mechanical bonds, or any other suitable attachment means or combinations of these attachment means as are known in the art.

FIG. 2 illustrates one use of hook-and-loop fastening systems. This particular use is a commercially important use of such systems and will be used for convenience in this specification to illustrate the present invention. It is to be understood that the present invention can be used in other applications, and no such applications are disclaimed.

The present invention is concerned with the loop structure portions of hook-and-loop fastening systems. From even a cursory examination of FIG. 2, those skilled in the art can readily deduce two requirements for loop structures. First, loop structure 2 must be able to cooperate with hook structure 3 to effectively releasably secure diaper 21 about the wearer. Second, one skilled in the art would recognize that diaper 21 must be capable of being made at high speed if it is to be commercially viable. This recognition leads to the requirement that loop structure 2 must be such that it can be affixed to diaper 21 in a high speed manufacturing process in a condition such that it will function effectively in cooperating with hook structure 3. The last words of the foregoing sentence are emphasized to indicated that mere high speed application of loop element 2 to diaper 21, while necessary, is not in and of itself sufficient. After application, loop structure must be in condition for efficient, effective use.

Disposable diapers are made by well known processes (sometimes called "converting processes") at high speed. The particular process used, of course, depends on the design of the diaper and the materials used. In such processes, various components (topsheet, backsheet, hook structure, loop structure, etc.) are introduced into the process by being unwound from large rolls of the material in question. (These large rolls are sometimes called "parent rolls.") The converting processes operate at high speed so long as the various materials can be unwound at high speed. Obviously, each parent roll contains only a finite quantity of material. When the material on a parent roll is exhausted, the converting process must be either stopped completely or significantly slowed while a new parent roll of material is installed and the new supply of material is introduced into the converting process. In order to provide converting processes with high average rates of production, effort is expended in seeking ways to increase the amount of material on any given parent roll.

One obvious way of increasing the amount of material on a parent roll is to make larger parent rolls. That is to say, to make parent rolls having larger diameters. There are practical limits to the diameter of a parent roll, however. One such limit is the physical space available for a parent roll. This space is dictated by the particular orientation of the converting process and the process equipment involved.

A second limit is imposed on the diameter of a parent roll used for compressible materials. This limit is imposed because as the diameter of a parent roll increases, the pressure (or force per unit area) exerted on the material increases as the distance from the center of the parent roll decreases. Stated in another way: as material is wound onto a parent roll at any given tension, compressive forces are exerted on the material already on the roll. These forces are in general not uniform throughout the radius of the parent roll, but are greater nearer the center of the roll than nearer the surface of the roll. Winding more material onto the parent roll will, then, increase the compressive forces, particularly near the center of the roll. These increased compressive forces can represent a limitation on roll diameter when the material in question is deformed by the forces to such an extent that it will no longer perform its intended function effectively and efficiently in the article of manufacture.

Another obvious way to increase the amount of a compressible material on a parent roll of any given diameter is to increase the tension with which it is wound onto the roll, thereby compressing the material and decreasing the diameter of the parent roll for any given quantity of material. This method can suffer from the same limitation as expressed in the immediately preceding paragraph: increased compressive forces in the parent roll can deform the material to an unacceptable extent.

The present invention permits the preparation of parent rolls of loop structure material, which parent rolls have greater diameters than heretofore possible and which material can be wound onto the parent rolls at greater tension than heretofore possible. The net result of the greater diameters and higher tensions is the placement of greater quantities of loop structure material on the parent rolls thereby allowing longer intervals of uninterrupted converting process operation and, hence, faster overall production of disposable diapers. The invention is not concerned with the preparation of parent rolls which can be prepared by any means known to those skilled in the art. The invention is concerned with the treatment of the loop structure material as it is being introduced into the converting process.

The present invention is of a restoration process for the loop structure material after it is unwound from its parent roll. As used in this specification, "restore" is a verb meaning to remove deformations at least partially from the loop elements of a loop structure thereby returning the elements at least partially, in a practical sense, to their original orientation, and thereby enhancing their ability to cooperate with hook elements relative to the fully deformed state of the loop elements.

Figure 3:
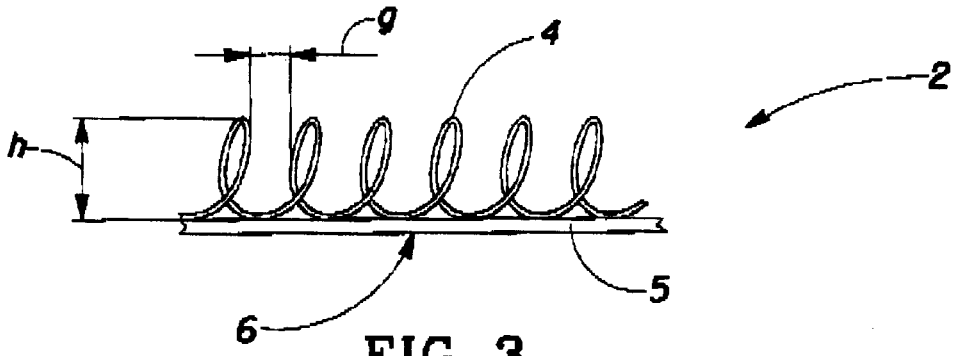
FIG. 3 is a cross sectional view of the generic loop structure portion of the generic hook-and-loop fastening system illustrated in FIG. 1. Certain dimensions have been indicated.

FIG. 3 is a cross sectional view of loop structure 2 illustrated in FIG. 1. As noted above, illustrated loop structure 2 and loop elements 4 are intended to represent a wide variety of such structures and elements while not illustrating any one structure or element with particularity. In FIG. 3, "h" indicates the average undeformed height of loop elements 4 and "g" indicates the average gap (i.e. the average spacing) between adjacent loop elements 4. Loop structures are sometimes supplied by the manufacturer as a "pre-glued" material. That is to say, the manufacturer of a loop structure will sometimes apply an article attachment adhesive (such as contact adhesive or hot melt adhesive) to loop structure attachment surface 6. The function of the attachment adhesives is, as the name implies, to attach the loop structure to the article being manufactured. In the present invention, loop structure 2 is free of attachment adhesive on loop structure attachment surface 6 until it loop elements 4 have been restored and loop structure 2 passes on into the converting process as described below.

Figure 4:
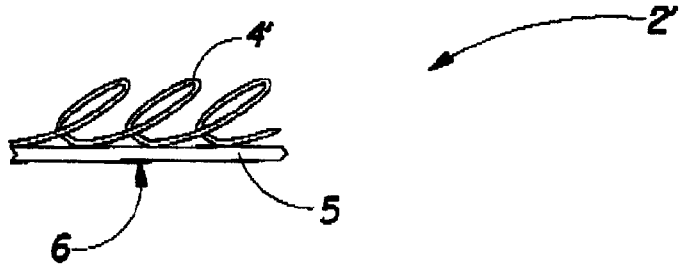
FIG. 4 is the cross sectional view of the generic loop structure illustrated in FIG. 3 in which the generic loop elements have been deformed.

FIG. 4 illustrates deformed loop structure 2'. Deformed loop structure 2' is loop structure 2 of FIG. 3 after loop elements 4 of FIG. 3 have been subjected to deforming forces such as the compressive forces present in a parent roll. Reference numeral 4' indicates deformed loop elements. The deformation of the loop elements is, in general, permanent after compression and deformation in the parent roll. Such deformation is deleterious because the deformed loops will not cooperate with the hook elements of the fastening system as effectively or efficiently as will loop elements having their original configuration.

The first step of the present invention is the deforming of at least one loop element of a loop structure (such as loop structure 2 of FIG. 3) by winding the loop structure upon it self to form a parent roll. Techniques of such winding are well known to those skilled in the art. The actual technique used is immaterial to the practice of the present invention. The width of the parent roll is determined by the width of the loop structure required by the converting process in which the loop structure will be used. In the general case, the width of the parent roll will be the final length of the loop structure (e.g. the landing zone) used on the article. The diameter of the parent roll is dictated by the physical dimensions and orientation of the converting equipment. The tension of the loop structure as it is wound into a parent roll is dictated by the permitted diameter of the parent roll, the desired quantity of loop structure to be incorporated into the parent roll, and the extent of deformation of the loop elements that can be tolerated.

The second step of the present invention is the unwinding of the loop structure with its deformed loop element (such as deformed loop structure 2' of FIG. 4) from the parent roll.

The third step of the present invention is restoring the deformed loop elements by contacting them with a mechanical restoration device.

The fourth step of the present invention is using the restored loop structure in a continuous converting process.

Figure 5:
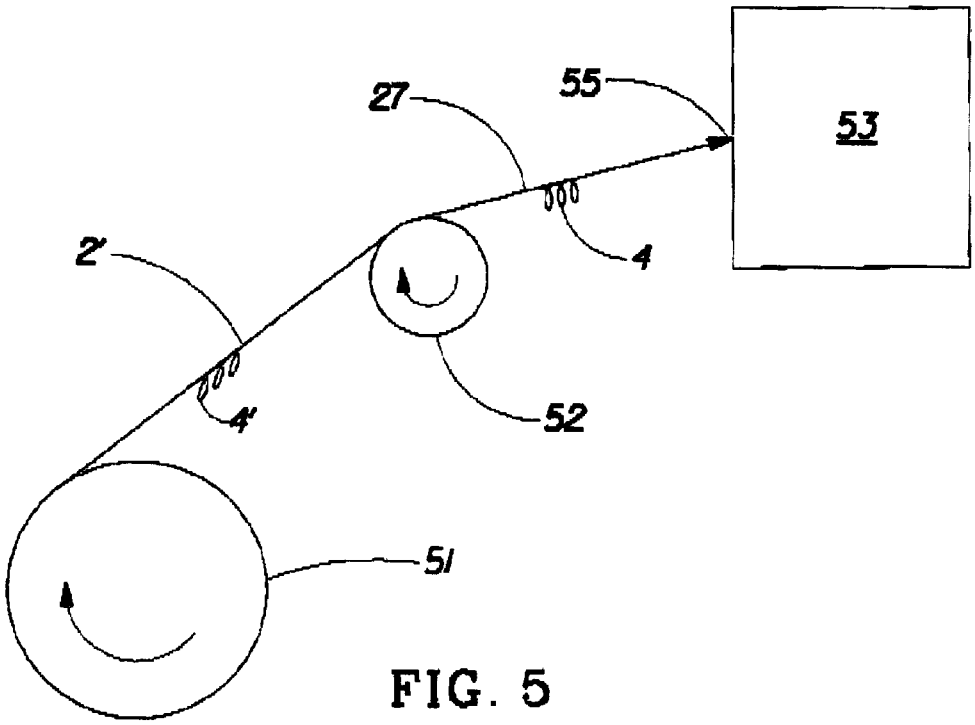
FIG. 5 is a schematic representation of the process of the present invention.

FIG. 5 is a schematic representation of the second, third, and fourth steps of the present invention.

A parent roll 51 containing deformed loop structure 2' is placed by any convenient technique on an unwind stand (not illustrated) well known to those skilled in the art. In the second step of the present invention, deformed loop structure 2' is unwound from parent roll 51 as parent roll 51 rotates in the direction indicated. Deformed loop elements 4' are oriented as shown. (The size of deformed loop elements 4' relative to other items in FIG. 5 is exaggerated for purposes of illustration.) In the third step of the present invention loop elements 4' are contacted with mechanical restoration device 52. During this contact, deformed loop elements 4' are restored to their undeformed state as loop elements 4 and deformed loop structure 2' is restored to loop structure 2. In the fourth step of the present invention, and as indicated by arrow 55, loop structure 2 is introduced into converting process 53.

Converting process 53 can be any convenient process in which loop structures are used in the manufacture of articles such as disposable diapers. For purposes of the present invention, the details of converting process 53 are immaterial.

FIG. 5 suggests that mechanical restoration device 52 is in the form of a roller rotating in the direction indicated. That is the preferred design and the preferred rotation, but not the only design or only rotation for mechanical restoration device 52. For example, the mechanical restoration device could be in the form of a substantially flat plate over which deformed loop structure 2' passes. (See FIG. 8 and FIG. 9 and the discussion below.)

FIG. 5 is a schematic representation. Various auxiliary mechanical and electronic elements which facilitate the implementation of the process of the present invention are not illustrated. For example, the unwind stand mentioned above, various drive and support mechanisms for parent roll 51 and mechanical restoration device 52, guide rolls for loop structures 2 and 2', various other supports, speed controls, and the like are neither illustrated nor specified. Those skilled in the art can readily select these auxiliary elements.

Figure 6:
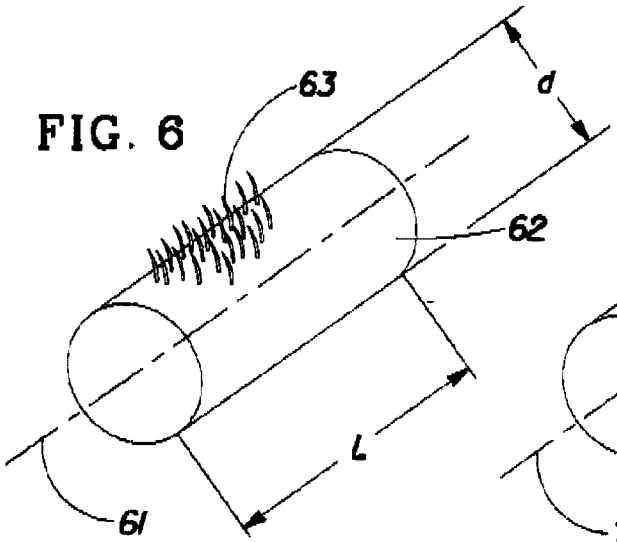
FIG. 6 is a perspective view of a preferred mechanical restoration device used in the present invention.

In a preferred embodiment of the present invention, mechanical restoration device 52 is a rotating brush in the form of a cylinder as illustrated in FIG. 6. Cylindrical rotating brush 62 has a diameter d and a length L; it rotates about axis of rotation 61. The outer surface of brush 62 is provided with a plurality of bristles 63. (Only a small portion of bristles 63 on the surface of brush 62 are illustrated.) Preferably, bristles 63 are round. The length, diameter, and material of construction of bristles 63 are all determined by the nature of the loop elements concerned. Preferably, bristles 63 have a free length greater than about loop height h shown in FIG. 3. The free length of a bristle is the distance from the free tip of the bristle to the surface to which the bristle is attached. Preferably, the average bristle free length is less than about 3h (i.e. less than about three times the average undeformed height of loop elements 4 as shown in FIG. 3). The material of construction of the bristles can be readily selected so that restoration and not tearing of the loop elements occurs. The bristles are selected sot hat the average bristle will itself bend rather than tear a loop element. Preferably, bristles 63 have an average bending modulus of less than yield strength of the loop elements.

The spatial arrangement of bristles 63 on mechanical restoration 62 device is not critical so long as there are enough bristles present to adequately contact, during restoration, the deformed loop elements of the particular deformed loop structure in question. Length L and diameter d of mechanical restoration device 63 are not critical to the practice of the present invention and can be convenient dimensions readily selected by those skilled in the art.

Figure 7:
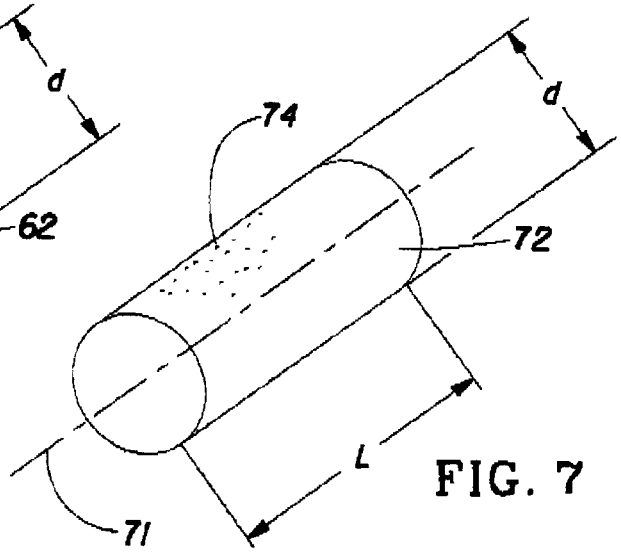
FIG. 7 is a perspective view of an alternate preferred mechanical restoration device used in the present invention.

Alternatively, the mechanical restoration device of the present invention can be a rotating cylinder as illustrated in FIG. 7. In this alternate preferred embodiment of the present invention, mechanical restoration device 52 is a rotating cylinder as illustrated in FIG. 7. Rotating cylinder 72 has a diameter "d" and a length "L;" it rotates about axis of rotation 71. Cylinder 72 is provided with a scarfing surface 74. Scarfing surface 74 has a roughness of at least about 500 RMS.

Surface roughness is measured in accordance with American National Standard ANSI/ASME B46.1-1985.

Length L, diameter d, and the material of construction of cylinder 72 are not critical to the practice of the present invention and can be convenient dimensions and materials readily selected by those skilled in the art.

Figure 8:
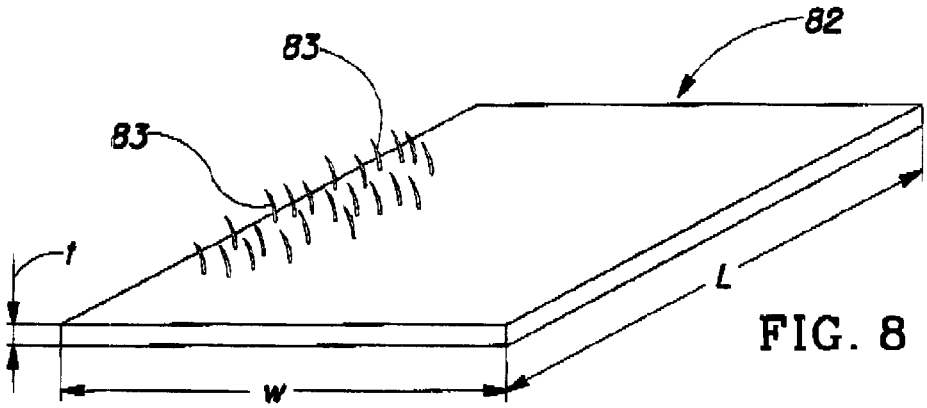
FIG. 8 is a perspective view of an alternate preferred mechanical restoration device used in the present invention.
Figure 9:
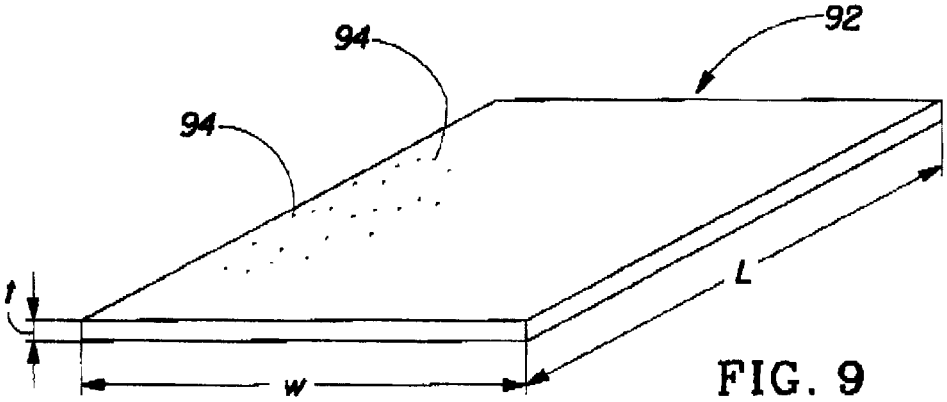
FIG. 9 is a perspective view of an alternate preferred mechanical restoration device used in the present invention.

The two preferred mechanical restoration devices described above are in the form of a rotating brush and a rotating cylinder. Alternatively, the mechanical restoration device can be in the form of a substantially flat brush or a substantially flat plate as shown in FIG. 8 and FIG. 9. For the purposes of the present invention, a brush or a plate is substantially flat if the portion in contact with the deformed loop elements is curved, but subtends an arc of less than about 180°. The substantially flat brush and the substantially flat plate can be stationary or can move with respect to the deformed loop structure in contact with it.

In FIG. 8, mechanical restoration device 82 is illustrated as a substantially flat brush provided with a plurality of bristles 83. Preferably, bristles 83 have a length greater than about loop height h shown in FIG. 3. Preferably, bristle length is less than about 3h. Preferably, bristles 83 have a diameter less than about 2g (i.e. less than about twice the average gap between loop elements 4 as shown in FIG. 3). The material of construction of the bristles can be readily selected so that restoration and not tearing of the loop elements occurs. Preferably, bristles 83 have a modulus of less than the modulus of elasticity of the loop elements. The spatial arrangement of bristles 83 on mechanical restoration 82 device is not critical so long as there are enough bristles present to adequately contact, during restoration, the deformed loop elements of the particular deformed loop structure in question. Length L, width w, and thickness t of mechanical restoration device 83 are not critical to the practice of the present invention and can be convenient dimensions readily selected by those skilled in the art. In use, mechanical restoration device 83 is substituted for mechanical restoration device 52 as illustrated in FIG. 5

In FIG. 9, mechanical restoration device 92 is illustrated as a substantially flat plate with a scarfing surface 94. Scarfing surface 94 has a roughness of at least about 500 RMS. Length L, width w, thickness t, and the material of construction of mechanical restoration device 92 are not critical to the practice of the present invention and can be convenient dimensions and materials readily selected by those skilled in the art. In use, mechanical restoration device 92 is substituted for mechanical restoration device 52 as illustrated in FIG. 5

EXAMPLES

The following examples are presented by way of illustration and not by way of limitation.

Example One

Loop structure material (hereinafter referred to as the "loop web") denominated EBL (XPL-7034) and comprising polypropylene loop elements affixed to a polyethylene loop support structure is obtained from The Minnesota Mining and Manufacturing Company, Personal Care and Related Products Division, of St. Paul, Minn. The loop web has an original thickness of about 0.381 mm, which includes a loop element height of about 0.30 mm. This loop web, 178 mm wide, is wound upon itself to form a parent roll of loop web material; the loop elements are oriented toward the center (i.e. axis) of the parent roll. The parent roll has an initial finished diameter of about 81.3 cm. The loop web is wound upon itself at a tension of about 35.4 kg per m of width of loop web. The loop elements of the loop web are deformed from their original upright orientation to such an extent that the average thickness of the loop web on the parent roll is about 380 microns.

The parent roll of loop web is placed into a loop restoration system having the general orientation illustrated in FIG. 5. It is to be understood that various support and drive elements, well known to those skilled in the art, are not shown in FIG. 5. More specifically, the parent roll is placed in an unwind stand where the loop web is unwound at a liner speed of about 24.7 m per min and directed toward a mechanical restoration device. In this Example One, the mechanical restoration device comprises a rotating cylindrical brush provided with a plurality of bristles. The overall diameter of the cylindrical brush, from bristle tip to bristle tip, is about 7.6 cm and the cylindrical brush is about 200 mm long. The average bristle in the cylindrical brush has an average free length of about 10 mm. The cylindrical brush is mechanically driven so that its surface moves in the direction of the moving loop web, and the surface of the cylindrical brush is driven at a linear speed of abut 24.7 m per min. The loop web contacts the surface of the cylindrical brush through an angle of about 20°. During the passage of the loop web over the mechanical restoration device, the deformed loop elements associated with the loop web are restored essentially to their original upright orientation and are rendered suitable for use in the manufacture of disposable diapers. After leaving the mechanical restoration device of this Example One, the loop web, with its now-restored loop elements, is used in the manufacture of disposable diapers according to the teaching of Buell in the hereinbefore mentioned U.S. Pat. No. 5,221,274.

Example Two

Example One is repeated except that the mechanical restoration device comprises a cylinder, about 7.6 cm in diameter and 200 mm long, provided with a scarfing surface. This surface has a roughness of about 500 and is provided by Plasma Coating of Tennessee, Inc. of Memphis, Tenn. This surface is denominated 936 and comprises a polymer having Teflon® polytherthalatefluroethylene grit embedded therein. In this Example Two, the cylinder (i.e. the mechanical restoration device) is mechanically driven so that its surface moves counter to the direction of movement of the loop web and at a speed of about 12 m per min. As in Example One, the deformed loop elements are restored essentially to their original upright orientation, and the loop web, with its now-restored loop elements, is used in the manufacture of disposable diapers according to the teaching of Buell in the hereinbefore mentioned U.S. Pat. No. 5,221,274.

What is claimed is:

1. In a process for the manufacture of an article comprising a hook-and-loop fastening system, the improvement comprising the steps of:

a) Providing a loop structure comprising a plurality of loop elements, said loop elements being affixed to a support substrate, said support substrate being substantially free of article attachment adhesives;

b) Deforming at least a portion of said loop elements by winding said loop structure upon itself to form a parent roll;

c) Unwinding said loop structure from said parent roll;

d) Restoring at least a portion of said deformed loop elements by contacting said deformed loop elements with a mechanical restoration device;

e) Providing an article; and f) Introducing said loop structure comprising said restored loop elements onto the article.

2. The process of claim 1 wherein said mechanical restoration device comprises a brush.

3. The process of claim 2 wherein said brush comprises a rotating cylinder.

4. The process of claim 2 wherein said brush is a substantially flat brush.

5. The process of claims 2, 3, or 4 wherein said brush comprises a plurality of bristles, said bristles having an average free length greater than about three times the average undeformed height of said loop elements.

6. The process of claim 5 wherein said bristles have an average bending modulus less than the average modulus of elasticity of said loop elements.

7. The process of claim 1 wherein said mechanical restoration device comprises a rotating cylinder provided with a scarfing surface.

8. The process of claim 1 wherein said mechanical restoration device comprises a substantially flat plate provided with a scarfing surface.

* * * * *